(12) United States Patent
Thies

(10) Patent No.: US 8,546,101 B2
(45) Date of Patent: Oct. 1, 2013

(54) COMPOUND SCREENING USING CHONDROCYTES DERIVED FROM PRIMATE PLURIPOTENT STEM CELLS

(75) Inventor: R. Scott Thies, Pleasanton, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 13/021,497

(22) Filed: Feb. 4, 2011

(65) Prior Publication Data

US 2011/0129867 A1   Jun. 2, 2011

Related U.S. Application Data

(60) Division of application No. 11/345,878, filed on Feb. 1, 2006, now Pat. No. 7,906,330, which is a continuation of application No. 10/313,740, filed on Dec. 6, 2002, now abandoned.

(60) Provisional application No. 60/339,043, filed on Dec. 7, 2001.

(51) Int. Cl.
*C12Q 1/02* (2006.01)
*C12N 5/02* (2006.01)

(52) U.S. Cl.
USPC .............................. 435/29; 435/375; 435/383

(58) Field of Classification Search
None
See application file for complete search history.

(56) References Cited

U.S. PATENT DOCUMENTS

| | | | |
|---|---|---|---|
| 4,439,521 A | 3/1984 | Archer et al. | |
| 4,797,213 A | 1/1989 | Parisius et al. | |
| 5,843,780 A | 12/1998 | Thomson | |
| 5,888,816 A | 3/1999 | Coon et al. | |
| 5,908,784 A | 6/1999 | Johnstone et al. | |
| 5,919,703 A | 7/1999 | Mullen et al. | |
| 6,090,622 A | 7/2000 | Gearhart et al. | |
| 6,150,163 A | 11/2000 | McPherson et al. | |
| 6,174,333 B1 | 1/2001 | Kadiyala et al. | |
| 6,200,806 B1 | 3/2001 | Thomson | |
| 6,326,201 B1 | 12/2001 | Fung et al. | |
| 6,800,480 B1 | 10/2004 | Bodnar et al. | |
| 7,029,913 B2 | 4/2006 | Thomson | |
| 7,297,539 B2 | 11/2007 | Mandalam et al. | |
| 2001/0005592 A1 | 6/2001 | Bhatnagar et al. | |
| 2002/0004225 A1 | 1/2002 | Hart et al. | |
| 2002/0005205 A1 | 1/2002 | Barry et al. | |

FOREIGN PATENT DOCUMENTS

| | | |
|---|---|---|
| WO | WO-96/18728 | 6/1996 |
| WO | WO-96/28539 | 9/1996 |
| WO | WO-98/04681 | 2/1998 |
| WO | WO-98/55594 | 12/1998 |
| WO | WO-99/20741 | 4/1999 |
| WO | WO-00/27996 | 5/2000 |
| WO | WO-00/47721 | 8/2000 |
| WO | WO-00/72885 | 12/2000 |
| WO | WO-00/78929 | 12/2000 |
| WO | WO-01/08610 | 2/2001 |
| WO | WO-01/39784 | 6/2001 |
| WO | WO-01/51616 | 7/2001 |
| WO | WO-01/77300 | 10/2001 |
| WO | WO-01/80865 | 11/2001 |

OTHER PUBLICATIONS

Bonham et al. Race and Ethnicity in the Genome Era: The Complexity of the Constructs. American Psychologist, 2005, vol. 60, pp. 9-15.*
Olee et al. IL-18 Is Produced by Articular Chondrocytes and Induces Proinflammatory and Catabolic Responses. Journal Immunology, 1999, vol. 162, pp. 1096-1100.*
Nishida et al. Antisense Inhibition of Hyaluronan Synthase-2 in Human Articular Chondrocytes Inhibits Proteoglycan Retention and Matrix Assembly. Journal Biological Chem., 1999, vol. 274, pp. 21893-21899.*
Egerbacher et al. Ciprofloxacin causes cytosketetal chancges and detachment of human and rat chondrocytes in vitro. Arch. Toxicol, 2000, vol. 73, pp. 557-563.*
Ahn, J. et al., "Identification of the genes differently expressed in human dendritic cell subsets by cDNA subtraction and microarray analysis," *Blood 100*, (2002), pp. 1742-1754.
Amit, M. et al., "Clonally Derived Human Embryonic Stem Cell Lines Maintain Pluripotency and Proliferative Potential for Prolonged Periods of Culture," *Dev. Biol. 227*, (2000), pp. 271-278.
Assady, S. et al., "Insulin Production by Human Embryonic Stem Cells," *Diabetes 50*, (2001), pp. 1691-1697.
Bain, G. et al., "Embryonic Stem Cells Express Neuronal Properties in Vitro," *Dev. Bio. 168*, (1995), pp. 342-357.
Bodnar, A. et al., "Extension of life-span by introduction of telomerase into normal human cells," *Science 279*, (1998), pp. 349-352.
Bretzel, R. et al., "Islet Transplantation: Present Clinical Situation and Future Aspects," *Diabetes 109*(Suppl. 2), (2001), pp. S384-S399.
Brittberg, M. "Autologous Chondrocyte Transplantation," *Clin Orthop Related Res 367S*, (1999), p. S147-S155.
Buttery, L. et al., "Differentiation of osteoblasts and in vitro bone formation from murine embryonic stem cells," *Tissue Eng. 7*, (2001), pp. 89-99.
Chen, D. et al., "Bone morphogenetic protein," *Growth Factors 22*(4), (2004), pp. 233-241.
Connor, J. et al., "Human Cartilage Glycoprotein 39 (HC gp-39) mRNA Expression in Adult and Fetal Chondrocytes, Osteoblasts and Osteocytes by In-Situ Hybridization," *Osteoart. Cartilage 8*, (2000), pp. 87-95.

(Continued)

*Primary Examiner* — Deborah Crouch
(74) *Attorney, Agent, or Firm* — Law Office of Salvatore Arrigo and Scott Lee, LLP

(57) ABSTRACT

This invention provides a system for obtaining cells of the chondrocyte lineage by differentiating primate pluripotent stem cells. The process involves culturing the cells as a micromass or other aggregate form in a cocktail of differentiation agents that facilitates outgrowth of the desired cell type. Progeny are capable of synthesizing Type II collagen or aggrecan, or other products that are characteristic of the chondrocyte lineage. Chondrocytes and chondrocyte precursor cells obtained according to this disclosure are suitable for use in both research and clinical therapy.

22 Claims, No Drawings

(56) References Cited

OTHER PUBLICATIONS

Deutsch, G. et al., "A Bipotential Precursor Population for Pancreas and Liver Within the Embryonic Endoderm," *Development 128*, (2001), pp. 871-881.

Francis-West, P. et al., "BMP/GDF-Signalling Interactions During Synovial Joint Development," *Cell Tissure Res. 296*, (1999), pp. 111-119.

Gilbert, S. *Developmental Biology, Seventh Edition, Sinauer Associates, Inc., Sunderland. MA*, (2003), p. 465.

Grigolo, B. et al., "Transplantation of Chondrocytes Seeded on a Hyaluronan Derivative (Hyaff®-11) Into Cartilage Defects in Rabbits," *Biomaterials 22*, (2001), pp. 2417-2424.

Grover, J. et al., "Versican gene expression in human articular cartilage and comparison of mRNA splicing variation with aggrecan," *Biochem J. 291*(Pt. 2), (1993), pp. 361-367.

Hegert, C. et al., "Differentiation Plasticity of Chondrocytes Derived from Mouse Embryonic Stem Cells," *J. Cell Sci. 115*, (2002), pp. 4617-4628.

Heng, B., et al., "Directing stem cell differentiation into the chondrogenic lineage in vitro," *Stem Cells 22*(7), (2004), pp. 1152-1167.

Hoffmann, A. et al., "BMP Signaling Pathways in Cartilage and Bone Formation," *Crit. Rev. Eukaryotic Gene Expr. 11*(1-3), (2001), pp. 23-45.

Hunziker, E. et al., "Chondrogenesis in Cartilage Repair is Induced by Members of the Transforming Growth Factor-Beta Superfamily," *Clin. Ortho. Related Res. 391S*, (2001), pp. S171-S181.

Hwang, N. et al., "Chondrogenic Differentiation of Human Embryonic Stem Cell-Derived Cells in Arginine-Glycine-Aspartate-Modified Hydrogels," *Tiss. Eng. 12*(9), (2006), pp. 2695-2705

Jacobson, L. et al., "Differentiation of Endoderm Derivatives, Pancreas and Intestine, from Rhesus Embryonic Stem Cells," *Transpl. Proc. 33*, (2001), p. 674.

Jakob, M. et al., "Specific Growth Factors During the Expansion and Redifferentiation of Adult Human Articular Chondrocytes Enhance Chondrogenesis and Cartilaginous Tissue Formation in Vitro," *J. Cell. Biochem. 81*, (2001), pp. 368-377.

Jimenez, S. et al., "Characterization of human type II procollagen and collagen-specific antibodies and their application to the study of human type II collagen processing and ultrastructure," *Matrix Biology 16*, (1997), pp. 29-39.

Jorgensen, C. et al., "Stem Cells for Repair of Cartilage and Bone: The Next Challenge in Osteoarthritis and Rheumatoid Arthritis," *Ann. Rheum. Dis. 60*, (2001), pp. 305-309.

Kim, S, et al., "Intercellular Signals Regulating Pancreas Development and Function," *Genes Dev. 15*, (2001), pp. 111-127.

Kim, S. et al., "Musculoskeletal Differentiation of Cells Derived from Human Embryonic Germ Cells," *Stem Cells 23*, (2005), pp. 113-123.

Koay, E. et al., "Tissue engineering with chondrogenically differentiated human embryonic stem cells," *Stem Cells 25*, (2007), pp. 2183-2190.

Kolettas, E. et al., "Expression of cartilage-specific molecules is retained on long-term culture of human articular chondrocytes," *J. Cell Sci. 108*(Pt. 5), (1995) pp. 1991-1999.

Kondaiah, P. et al., "Identification of a novel transforming growth factor-beta (TGF-beta5) mRNA in *Xenopus laevis*," *J. Biol. Chem. 265*(2), (1990), pp. 1089-1093.

Kramer, J. et al., "Embryonic stem cell-derived chondrogenic differentiation in vitro; Activation by BMP-2 and BMP-4," *Mech. Dev. 92*(2), (2000), pp. 193-205.

Kumar, D. et al., "Transforming growth factor-Beta2 enhances differentiation of cardiac myocytes from embryonic stem cells," *Biochem. Biophys. Res. Comm. 332*, (2005), pp. 135-141.

Li, F. et al., "Bone morphogenetic protein 4 induces efficient hematopoietic differentiation of rhesus monkey embryonic stem cells in vitro," *Blood 98*, (2001), pp. 335-342.

Liechty, K. et al., "Human mesenchymal stem cells engraft and demonstrate site-specific differentiation after in utero transplantation in sheep." *Nature Med. 6*, (2000) pp. 1282-1286.

Lim, J. et al., "Proteosome analysis of conditioned medium from mouse embryonic fibroblast feeder layers which support the growth of human embryonic stem cells," *Proteomics 2*, (2002) pp. 1187-1203.

Lumelsky, N. et al., "Differentiation of Embryonic Stem Cells to Insulin-Secreting Structures Similar to Pancreatic Islets," *Science 292*, (2001), pp. 1389-1394.

Martin, I. et al., "Enhanced Cartilage Tissue Engineering by Sequential Exposure of Chondrocytes to FGF-2 During 2D Expansion and BMP-2 During 3D Cultivation," *J. Cell. Biochem. 83*,(2001), pp. 121-128.

Matsuda, T. et al., "STAT3 Activation is Sufficient to Maintain an Undifferentiated State of Mouse Embryonic Stem Cells," *EMBO J. 18*, (1999), pp. 4261-4269.

McKay, R. "Stem Cells in the Central Nervous System," *Science 276*, (1997), pp 66-71.

Minina, E. et al., "BMP and Ihh/PTHrP Signaling Interact to Coordinate Chondrocyte Proliferation and Differentiation," *Development 128*, (2001), pp. 4523-4534.

Niida, H. et al., "Severe Growth Defect in Mouse Cells Lacking the Telomerase RNA Component," *Nat. Genet. 19*, (Jun. 1998), pp. 203-206.

Oberholzer, J. et al., "Clinical Islet Transplantation: A Review," *Ann. NY Acad. Sci. 875*, (1999), pp. 189-199.

Ocelus, S. "Autologous Cultured Chondrocytes for the Treatment of Knee Cartilage Injury," *Ortho, Nursing 19*(4), (2000), pp. 19-28.

Odorico, J. et al., "Multilineage differentiation from human embryonic stem cell lines," *Stem Cells 19*, (2001), pp. 193-204.

Odorico, J. et al., "Pancreatic Gene Expression in Differentiating Embryonic Stem Cells," *Keystone Symposium Abstract*, (2000). p. 76.

Ofek, G, et al., "Mechanical characterization of differentiated human embryonic stem cells," *J. Biomechnical Eng. 131*,(2009), pp. 1-8.

Pateder, D. et al., "PTHrP Expression in Chick Sternal Chondrocytes is Regulated by TGF-beta Through Smad-Mediated Signaling," *J. Cell Physiol. 188*, (2001), pp. 343-351.

Peck, A. et al., "Pancreatic Stem Cells: Building Blocks for a Better Surrogate Islet to Treat Type 1 Diabetes," *Ann. Med. 33*, (2001), pp. 186-192.

Pereira, R. et al., "Cultured Adherent Cells from Marrow Can Serve as Long-Lasting Precursor Cells for Bone, Cartilage, and Lung in Irradiated Mice," *Proc. Natl. Acad. Sci. USA 92*, (1995), pp. 4857-4861.

Schuldiner, M. et al., "Effects of eight growth factors on the differentiation of cells derived from human embryonic stem cells," *Proc. Natl. Acad. Sci. USA 97*(21), (2000), pp. 11307-11312.

Shamblott, M. et al., "Derivation of pluripotent stem cells from cultured human primordial germ cells," *Proc. Natl. Acad. Sci. USA 95*, (1998), pp. 13726-13731.

Soria, B. et al., "Insulin-Secreting Cells Derived from Embryonic Stem Cells Normalize Glycemia in Streptozotocin-Induced Diabetic Mice," *Diabetes 49*(2), (2000), pp. 157-162.

Springer, I. et al., "Culture of cells gained from temporomandibular joint cartilage on non-absorbable scaffolds," *Biomaterials 22*(18), (2001), pp. 2569-2577.

St. Jacques, B. et al., "Indian hedgehog signaling regulates proliferation and differentiation of chondrocytes and is essential for bone formation," *Genes Dev. 13*, (1999), pp. 2072-2086.

Stokes, D. et al., "Regulation of type-II collagen gene expression during human chondrocyte de-differentiation and recovery of chondrocyte-specific phenotype in culture involves Sry-type high-mobility-group box (SOX) transcription factors," *Biochem. J. 360*(Pt. 2), (2001), pp. 461-470.

Teitelman, G. "On the Origin of Pancreatic Endocrine Cells, Proliferation and Neoplastic Transformation," *Tumour Biol. 14*, (1993), pp. 167-173.

Ten Koppel, P. et al., "A New in Vivo Model for Testing Cartilage Grafts and Biomaterials: The 'Rabbit Pinna Punch-Hole' Model," *Biomaterials 22*, (2001), pp. 1407-1414.

Thomson, J. et al., "Embryonic stem cell lines derived from human blastocysts," *Science 282*, (1998), pp. 1145-1147.

Thomson, J. et al., "Isolation of a primate embryonic stem cell line," *Proc. Natl. Acad. Sci. USA 92*, (1995), pp. 7844-7848.

Tsai, C. et al., "Estradiol-Induced Knee Osteoarthrosis in Ovariectomized Rabbits," *Clin. Orthop. Related Res. 291*, (1993), pp. 295-302.

Wall, N. et al., "TGF-beta Related Genes in Development," *Curr. Op. Genet. Dev. 4*, (1994), pp. 517-522.

Wobus, A. et al., "Retinoic acid accelerates embryonic stem cell-derived cardiac differentiation and enhances development of ventricular cardiomyocytes," *J. Mol. Cell Cardiol. 29*, (1997), pp. 1525-1539.

Wobus, A. et al., "Specific effects of nerve growth factor on the differentiation pattern of mouse embryonic stem cells in vitro," *Biomed. Biochim. Acta 47*(12), (1988), pp. 965-973.

Wu, Q. et al,, "Indian Hedgehog is an Essential Component of Mechanotransduction Complex to Stimulate Chondrocyte Proliferation," *J. Biol. Chem. 276*(38), (2001), pp. 35290-35296.

Xu, C. et al,, "Characterization and enrichment of cardiomyocytes derived from human embryonic stem cells," *Circ. Res. 91*(6), (2002), pp. 501-508.

Xu, C. et al., "Feeder-free growth of undifferentiated human embryonic stem cells," *Nature Biotech. 19*, (2001), pp. 971-974.

Xu, R. et al,, "Basic FGF and suppression of BMP signaling sustain undifferentiated proliferation of human ES cells," *Nat. Methods 2*(3), (2005), pp. 185-190.

Yamaoka, T. et al., "Development of Pancreatic Islets (Review)," *Int. J. Mol. Med. 3*, (1999), pp. 247-261.

Ying, Q. et al., "BMP induction of ld proteins suppresses differentiation and sustains embryonic stem cell self-renewal in collaboration with STAT3," *Cell 115*, (2003), pp. 281-292.

Yoo, J. et al., "Autologous Engineered Cartilage Rods for Penile Reconstruction," *J. Urol. 162*, (1999), pp. 1119-1121.

Zulewski, H. et al., "Muiltipotetial Nestin-Positive Stem Cells Isolated from Adult Pancreatic Islets Differentiate ex Vivo into Pancreatic Endocrine, Exocrine, and Hepatic Phenotypes, " *Diabetes 50*,(2001), pp. 521-533.

Zur Nieden, N. et al., "Induction of chondro-, osteo- and adipogenesis in embryonic stem cells by bone morphogenetic protein-2: Effect of cofactors on differentiating lineages," *BMC Dev. Biol. 5*(1), (2005), pp, 1-15.

Levy, S. et al., "The diploid genome sequence of an individual human", *PLoS Biol. 5*(10), (2007), pp. 2113-2144.

Verlinsky,Yuri, et al., JAMA, vol. 285, No. 24, pp. 3130-3133 (2001).

Vogel, Gretchen, Science, vol. 287, No. 5455, pp. 948-949 (2000).

Vogel, Gretchen, Science, vol. 289, No. 5484, pp. 1442-1443 (2000).

\* cited by examiner

COMPOUND SCREENING USING CHONDROCYTES DERIVED FROM PRIMATE PLURIPOTENT STEM CELLS

REFERENCE TO RELATED APPLICATIONS

This application is a divisional of and claims the right of priority to U.S. application Ser. No. 11/345,878, filed Feb. 1, 2006, issued as U.S. Pat. No. 7,906,330, which is a continuation of and claims the right of priority to U.S. application Ser. No. 10/313,740, filed Dec. 6, 2002 (abandoned), which claims priority to U.S. Provisional Application No. 60/339,043, filed Dec. 7, 2001. The priority documents are hereby incorporated by reference in their entirety along with International Patent Publication No. WO 03/050250.

TECHNICAL FIELD

This invention relates generally to the fields of cell biology, embryonic stem cells, and cell differentiation. Disclosed are differentiated cells from a novel source that have characteristics of chondrocytes.

BACKGROUND

Cartilage degradation is a hallmark of two disease groups: osteoarthritis, a degenerative condition, and rheumatoid arthritis, which is primarily caused by inflammation. The degradation leads to joint pain and mobility impairment to a degree that can be considerably disabling.

Over the last two decades, considerable progress have been made in the development of anti-inflammatory agents effective for inhibiting the progress of disease. But where degradation has already taken place, new therapies are needed to assist in the regenerating of joint cartilage.

Recent efforts in the art of regenerative medicine have been directed at developing cell populations capable of repairing cartilage. International patent publication WO 96/18728 reports established lines of articular chondrocytes. WO 98/55594 reports methods for chondrocyte growth and differentiation. WO 00/27996 reports serum-free medium for chondrocyte like cells, comprising minimum essential medium, growth factors, lipids and amino acids. U.S. Pat. No. 6,150,163 (Genzyme) outlines chondrocyte media formulations and culture procedures, in which de-differentiated human articular chondrocytes are grown in a medium containing TGFβ and either insulin or. insulin-like growth factor.

Jorgensen et al. (Ann. Rheum. Dis. 60:305, 2001) reviews recent progress in stem cells for repair of cartilage and bone in arthritis. Jakob et al. (J. Cell. Biochem. 26:81, 2001) studied specific growth factors involved in expansion and redifferentiation of adult human articular chondrocytes that enhance chondrogenesis and cartilage formation. M. Brittberg (Clin. Orthop. 367 Suppl:S147, 1999) reviews current chondrocyte transplantation procedures in which pure chondrocytes or other mesenchymal cells are harvested autologously or as allografts from a healthy tissue source, expanded in vitro, and then implanted into the defect at high density.

Despite the initial success of these clinical methods, it is clear that current sources of chondrocytes are inadequate to treat most of the instances of cartilage degeneration that present themselves at the clinic.

Kramer et al. (Mech. Dev. 92:193, 2000) reported that mouse embryonic stem cells can be modulated with bone morphogenic proteins (BMP-2 and BMP-4) to produce cells that stained with Alcian blue, a feature of chondrocytes, and expressing the transcription factor scleraxis. Regrettably, the mouse model of embryonic stem cell development is its own peculiar case, and does not yield strategies for differentiation that are applicable to other species. In fact, there are very few other mammalian species from which pluripotent stem cells have been reproducibly isolated.

Only recently did Thomson et al. isolate embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be kept from differentiation simply by culturing with Leukemia Inhibitory Factor (LIF), human embryonic stem cells must be maintained under very special conditions (U.S. Pat. No. 6,200,806; WO 99/20741; WO 01/51616).

Accordingly, it is necessary to develop whole new paradigms to differentiate human pluripotent cells into fully functional differentiated cell types.

SUMMARY

This invention provides a system for efficient production of primate cells that have differentiated from pluripotent cells into cells of the chondrocyte lineage. Populations of cells are described that are considerably enriched for chondrocytes suitable for both research and clinical therapy.

One embodiment of the invention is a cell population containing chondrocytes, obtained by differentiating primate pluripotent stem (pPS) cells. Exemplary pPS cells are human embryonic stem cells. Chondrocyte lineage cells can be identified by the ability to synthesize Type II collagen or aggrecan from an endogenous gene. Preferably, the population contains a minimal proportion of cells that synthesize elastic cartilage, fibrocartilage, hypertrophic cartilage or bone.

Another embodiment of the invention is a population of chondrocyte progenitors that proliferates in an in vitro culture, obtained by differentiating pPS cells, and capable of forming progeny having the characteristics of mature chondrocytes. The chondrocyte progenitors are no longer pluripotent, but are committed to the chondrocyte development pathway. The proportion of undifferentiated pluripotent cells in the population is preferably minimized, and any residual undifferentiated cells are not the cells responsible for forming the chondrocytes upon further proliferation. Optionally, replication capacity of the stem cells can be improved by increasing telomerase activity.

Another embodiment of the invention is a method for obtaining the cell populations of this invention, comprising differentiating pPS cells (for example, by forming embryoid bodies), then culturing the differentiated cells with a mixture of chondrocyte differentiation factors, such as in a micromass culture. Suitable factors are described in more detail later on in this disclosure, and include transforming growth factors (TGF), fibroblast growth factors (FGF), growth and differentiation factors (GDF), bone morphogenic proteins (BMP), hedgehog proteins (HH), L-ascorbic acid, and parathyroid hormone-related protein (PTHrP).

Another embodiment of the invention is a method for producing cartilage by incubating a cell population of this invention under conditions where connective tissue proteins are produced. Another embodiment of the invention is a method of screening a compound for its ability to modulate chondrocyte growth, differentiation, or synthesis of cartilage components, by combining the compound with a cell population of the invention and determining its effect.

Another embodiment of the invention is a pharmaceutical composition for producing, repairing, or maintaining cartilage in vivo, containing a cell population of this invention—and the use of such medicaments for reconstructing cartilage in a subject, for example, in cosmetic surgery or the treatment of joint trauma, arthritis, or osteoarthritis.

These and other embodiments of the invention are further elucidated in the description that follows.

DETAILED DESCRIPTION

This invention solves the problem of generating large populations of human chondrocytes by showing how to efficiently differentiate them from pluripotent stem cells.

Pluripotent stem (pPS) cells such as human embryonic stem (hES) cells can be coaxed along the chondrocyte differentiation pathway by first initiating general differentiation, and then focusing the differentiation process by culturing in the presence of factors that facilitate outgrowth of chondrocytes. A strategy been developed that helps optimize the combination of factors that are useful in efficiently generating cells of the chondrocyte lineage. The techniques of this invention are oriented at producing a population of cells enriched for cells that are capable of modeling cartilage in vivo by the synthesis of such connective tissue components as Type II collagen and aggrecan.

The development of methods to efficiently produce chondrocytes from hES cells is important, because hES cells can be caused to proliferate indefinitely. Accordingly, this invention provides a system that can be used to generate unbounded quantities of chondrocytes.

The disclosure that follows provides a full description of how to make the chondrocytes of this invention. It provides extensive illustrations of how these cells can be used in research and pharmaceutical development. The disclosure also provides pharmaceutical compositions, devices, and treatment methods for the use of pPS derived chondrocytes for regeneration and remodeling of cartilage to restore joint mobility and for cosmetic purposes.

Definitions

For purposes of this disclosure, unless otherwise specified, the term "chondrocyte" refers to any cell from the chondrocyte cell pathway. This includes mature cells capable of modeling cartilage by the synthesis of Type II collagen and aggrecan. It also includes progenitor cells capable of self renewal that are committed to form mature chondrocytes.

In the context of cell ontogeny, the adjective "differentiated" is a relative term. A "differentiated cell" is a cell that has progressed further down the developmental pathway than the cell it is being compared with.

A "differentiation agent", as used in this disclosure, refers to one of a collection of compounds that are used in culture systems of this invention to produce differentiated cells of the chondrocyte lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others. It may also act as an inhibitor to other factors that may be in the medium or synthesized by the cell population that would otherwise direct differentiation down the pathway to an unwanted cell type.

Prototype "primate Pluripotent Stem cells" (pPS cells) are pluripotent cells derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice. The term includes both established lines of stem cells of various kinds, and cells obtained from primary tissue that are pluripotent in the manner described.

Included in the definition of pPS cells are embryonic cells of various types, exemplified by human embryonic stem (hES) cells, described by Thomson et al. (Science 282:1145, 1998); embryonic stem cells from other primates, such as Rhesus stem cells (Thomson et al., Proc. Natl. Acad. Sci. USA 92:7844, 1995), marmoset stem cells (Thomson et al., Biol. Reprod. 55:254, 1996) and human embryonic germ (hEG) cells (Shamblott et al., Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. The pPS cells are preferably not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells within the population will often be surrounded by neighboring cells that are differentiated.

"Feeder cells" or "feeders" are terms used to describe cells of one type that are co-cultured with cells of another type, to provide an environment in which the cells of the second type can grow. Certain types of pPS cells can be supported by primary mouse embryonic fibroblasts, immortalized mouse embryonic fibroblasts, or human fibroblast-like cells differentiated from hES cell. pPS cell populations are said to be "essentially free" of feeder cells if the cells have been grown through at least one round after splitting in which fresh feeder cells are not added to support the growth of pPS cells.

The term "embryoid bodies" is a term of art synonymous with "aggregate bodies", referring to aggregates of differentiated and undifferentiated cells that appear when pPS cells overgrow in monolayer cultures, or are maintained in suspension cultures. Embryoid bodies are a mixture of different cell types, typically from several germ layers, distinguishable by morphological criteria and cell markers detectable by immunocytochemistry.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

General Techniques

General aspects of the biology and pathology of cartilage, and the role of chondrocytes in the maintenance of joints can be found in the following reference textbooks: *Mechanobiology: Cartilage and Chondrocyte*, by J. F. Stoltz ed., IOS Press 2000; *Biological Regulations of the Chondrocytes*, by M. Adolphe ed., CRC Press 1992; *Bone and Cartilage Allografts*, by G. E. Friedlaender et al. eds., Amer. Acad. Orthopaedic 1991; *Joint Cartilage Degradation*, by J. F. Woessner & D. S. Howell eds., Marcel Dekker 1992; *Skeletal Tissue Mechanics*, $2^{nd}$ edition by R. B. Martin et al., Springer Verlag 1998; *Molecular and Developmental Biology of Cartilage*, B. De Crombrugghe et al. eds., Ann. N.Y. Acad. Sci. Vol. 785: 1996; and *Joint Structure and Function: A Comprehensive Analysis*, $3^{rd}$ edition by P. K. Levangie et al. eds, F A Davis, 2000.

Laboratory techniques useful in the practice of this invention can be found in standard textbooks and reviews in cell biology, tissue culture, and embryology. Stem cell biology and manipulation is described in *Teratocarcinomas and embryonic stem cells: A practical approach*, by E. J. Robertson ed., IRL Press Ltd. 1987; *Guide to Techniques in Mouse Development*, by P. M. Wasserman et al. eds., Academic Press 1993; *and Embryonic Stem Cell Differentiation in Vitro*, by M. V. Wiles, Meth. Enzymol. 225:900 1993.

Methods in molecular genetics and genetic engineering are described in *Molecular Cloning: A Laboratory Manual*, 2nd Ed., by Sambrook et al. 1989; *Oligonucleotide Synthesis*, by M. J. Gait ed. 1984; *Animal Cell Culture, by R. I. Freshney ed.* 1987; the series *Methods in Enzymology*, by Academic Press; *Gene Transfer Vectors for Mammalian Cells*, by J. M. Miller & M. P. Calos eds. 1987; *Current Protocols in Molecular Biology and Short Protocols in Molecular Biology, 3rd Edition*, by F. M. Ausubel et al. eds. 1987 & 1995; and *Recombinant DNA Methodology II*, by R. Wu ed., Academic Press 1995. Reagents, cloning vectors, and kits for genetic manipulation referred to in this disclosure are available from commercial vendors such as BioRad, Stratagene, Invitrogen, and ClonTech. General techniques used in raising antibodies, and the design and execution of immunoassays and immunohistochemistry, are found in the *Handbook of Experimental Immunology*, by D. M. Weir & C. C. Blackwell eds.; *Current Protocols in Immunology*, by J. E. Coligan et al. eds. 1991; and R. Masseyeff, W. H. Albert, and N. A. Staines eds., *Methods of Immunological Analysis*, by Weinheim: VCH Verlags GmbH 1993.

Sources of Stem Cells

This invention can be practiced using stem cells of various types. Amongst the stem cells suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells or embryonic germ cells, as exemplified below.

The techniques of this invention can also be implemented directly with primary embryonic or fetal tissue, deriving chondrocytes directly from primary cells that have the potential to give rise to chondrocytes without first establishing an undifferentiated cell line.

Embryonic Stem Cells

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000.

Briefly, human blastocysts are obtained from human in vivo preimplantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Fertil. Steril. 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (~200 U/mL; Gibco) or by selection of individual colonies by micropipette. Clump sizes of about 50 to 100 cells are optimal.

Embryonic Germ Cells

Human Embryonic Germ (hEG) cells can be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1mL 0.05% trypsin/0.53 mM sodium EDTA solution (BRL) and cut into <1 mm$^3$ chunks. The tissue is than pipetted through a 100 μL tip to further disaggregate the cells. It is incubated at 37° C. for ~5 min, then ~3.5 mL EG growth medium is added. EG growth medium is DMEM, 4500 mg/LD-glucose, 2200 mg/L mM NaHCO$_3$; 15% ES qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant bFGF (Genzyme); and 10 μM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced, incubated 1 h or overnight at 37° C., resuspended in 1-3 mL of EG growth medium, and plated onto a feeder layer.

Ninety-six well tissue culture plates are prepared with a sub-confluent layer of feeder cells (e.g., STO cells, ATCC No. CRL 1503) cultured for 3 days in modified EG growth medium free of LIF, bFGF or forskolin, inactivated with 5000 rad γ-irradiation. ~0.2 mL of primary germ cell (PGC) suspension is added to each of the wells. The first passage is done after 7-10 days in EG growth medium, transferring each well to one well of a 24-well culture dish previously prepared with irradiated STO mouse fibroblasts. The cells are cultured with daily replacement of medium until cell morphology consistent with EG cells is observed, typically after 7-30 days or 1-4 passages.

Propagation of pPS Cells in an Undifferentiated State pPS cells can be propagated continuously in culture, using culture conditions that promote proliferation without promoting differentiation. Exemplary serum-containing ES medium is made with 80% DMEM (such as Knockout DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Just before use, human bFGF is added to 4 ng/mL (WO 99/20741, Geron Corp.).

Traditionally, ES cells are cultured on a layer of feeder cells, typically fibroblasts derived from embryonic or fetal tissue. Embryos are harvested from a CF1 mouse at 13 days of pregnancy, transferred to 2 mL trypsin/EDTA, finely minced, and incubated 5 min at 37° C. 10% FBS is added, debris is allowed to settle, and the cells are propagated in 90% DMEM, 10% FBS, and 2 mM glutamine. To prepare a feeder cell layer, cells are irradiated to inhibit proliferation but permit synthesis of factors that support ES cells (~4000 rads γ-irradiation). Culture plates are coated with 0.5% gelatin overnight, plated with 375,000 irradiated mEFs per well, and used 5 h to 4 days after plating. The medium is replaced with fresh hES medium just before seeding pPS cells.

Scientists at Geron have discovered that pPS cells can be maintained in an undifferentiated state even without feeder cells. The environment for feeder-free cultures includes a suitable culture substrate, particularly an extracellular matrix such as Matrigel® or laminin. The pPS cells are plated at >15,000 cells cm$^{-2}$ (optimally 90,000 cm$^{-2}$ to 170,000 cm$^{-2}$). Typically, enzymatic digestion is halted before cells become completely dispersed (say, ~5 min with collagenase IV). Clumps of ~10 to 2,000 cells are then plated directly onto the substrate without further dispersal. Alternatively, the cells can be harvested without enzymes before the plate reaches confluence by incubating ~5 min in a solution of 0.5 mM EDTA in PBS. After washing from the culture vessel, the cells are plated into a new culture without further dispersal.

Feeder-free cultures are supported by a nutrient medium containing factors that support proliferation of the cells without differentiation. Such factors may be introduced into the medium by culturing the medium with cells secreting such factors, such as irradiated (~4,000 rad) primary mouse embryonic fibroblasts, telomerized mouse fibroblasts, or fibroblast-like cells derived from pPS cells. Medium can be conditioned by plating the feeders at a density of ~5-6×10$^4$ cm$^{-2}$ in a serum free medium such as KO DMEM supplemented with 20% serum replacement and 4 ng/mL bFGF. Medium that has been conditioned for 1-2 days is supplemented with further bFGF, and used to support pPS cell culture for 1-2 days. Alternatively or in addition, other factors can be added that help support proliferation without differentiation, such as ligands for the FGF-2 or FGF-4 receptor, ligands for c-kit (such as stem cell factor), ligands for receptors associated with gp130, insulin, transferrin, lipids, cholesterol, nucleosides, pyruvate, and a reducing agent such as β-mercaptoethanol. Features of the feeder-free culture method are further discussed in International Patent Publication WO 01/51616; and Xu et al., Nat. Biotechnol. 19:971, 2001.

Under the microscope, ES cells appear with high nuclear/cytoplasmic ratios, prominent nucleoli, and compact colony formation with poorly discernable cell junctions. Primate ES cells express stage-specific embryonic antigens (SSEA) 3 and 4, and markers detectable using antibodies designated Tra-1-60 and Tra-1-81 (Thomson et al., Science 282:1145, 1998). Mouse ES cells can be used as a positive control for SSEA-1, and as a negative control for SSEA-4, Tra-1-60, and Tra-1-81. SSEA-4 is consistently present on human embryonal carcinoma (hEC) cells. Differentiation of pPS cells in vitro results in the loss of SSEA-4, Tra-1-60, and Tra-1-81 expression, and increased expression of SSEA-1, which is also found on undifferentiated hEG cells.

Differentiating Pluripotent Cells Into Chondrocytes

Chondrocytes of this invention are obtained by culturing, differentiating, or reprogramming stem cells in a special growth environment that enriches for cells with the desired phenotype (either by outgrowth of the desired cells, or by inhibition or killing of other cell types). These methods are applicable to many types of stem cells, including primate pluripotent stem (pPS) cells described in the previous section.

When derived from an established line of pPS cells, the cell populations and isolated cells of this invention will have the same genome as the line from which they are derived. This means that over and above any karyotype abnormalities, the chromosomal DNA will be over 90% identical between the pPS cells and the chondrocytes, which can be inferred if the chondrocytes are obtained from the undifferentiated line through the course of normal mitotic division. Chondrocytes that have been treated by recombinant methods to introduce a transgene or knock out an endogenous gene are still considered to have the same genome as the line from which they are derived, since all non-manipulated genetic elements are preserved.

Initiating the Differentiation Process

It is a hypothesis of this invention that an efficient way to perform the derivation of chondrocytes from pPS cells is to initiate differentiation of the pPS cells in a non-specific manner, and then combine the initiated cells with chondrocyte-specific differentiation factors.

One alternative is to cause the pPS cells to form embryoid bodies or aggregates: for example, by overgrowth of a donor pPS cell culture, or by culturing pPS cells in suspension in culture vessels having a substrate with low adhesion properties that allows embryoid bodies to form. In an exemplary method, confluent monolayer cultures of hES cells are harvested by incubating in 1 mg/mL collagenase for 5-20 min, and dissociated into clusters. They are then plated in non-adherent cell culture plates (Costar) in a medium composed of 80% knockout DMEM (Gibco) and 20% non-heat-inactivated fetal bovine serum (Hyclone), supplemented with 1% non-essential amino acids, 1 mM glutamine, 0.1 mM β-mercaptoethanol. The embryoid bodies are fed every other day by the addition of 2 of medium per well.

As an alternative, the differentiation process can also be initiated by culturing in a non-specific differentiation paradigm: for example, by including retinoic acid (RA) or dimethyl sulfoxide (DMSO) in the culture medium. Another method to initiate differentiation by plating the undifferentiated pPS cells onto a substrate that stimulates the differentiation process, such as polyornithine. See International patent publication WO 01/51616.

Driving Differentiation Towards Chondrocytes

In order to direct the culture towards the chondrocyte pathway, pPS cells that have been initiated as described in the last section are cultured in a cocktail of chondrocyte differentiation factors. Alone or in combination, each of the factors may direct cells to differentiate down the chondrocyte pathway, cause outgrowth of cells with a chondrocyte phenotype, inhibit growth of other cell types, or enrich for chondrocytes in another fashion: it is not necessary to understand the mechanism resulting in chondrocytes being enriched in order to practice the invention.

Candidate components of the chondrocyte differentiation mix include transforming growth factors (especially TGFβ1, TGFβ2 and TGFβ3), fibroblast growth factors (especially basic fibroblast growth factor, FGF-2), growth and differentiation factors (especially GDF-5, GDF-6 and GDF-7), bone morphogenic proteins (especially BMP-2, BMP-4, BMP-5, BMP-6 and BMP-7), hedgehog proteins (especially Indian hedgehog, IHH), L-ascorbic acid, and parathyroid hormone-related protein (PTHrP). Gibco is a preferred source of basic FGF. Most of the other compounds are available from R&D Systems, Minneapolis Minn.

It is a hypothesis of this invention that the profile of signaling factors and their receptors change as differentiation proceeds, and the resultant cell populations are also changing with time. To screen potential chondrocyte differentiation factors, pPS cells can be cultured as aggregate bodies for various times from 0 to 10 days, to capture a broad range of differentiation stages for the second step of the protocol. At each of the time points, the initiated aggregates are disaggregated and replated in a medium containing a mixture of candidate factors.

It is also a hypothesis of this invention that differentiation of pPS cells into chondrocytes is enhanced if cells are kept in clusters. Interaction between cells in the clusters may be important to keep the cells from dedifferentiating, and routed along the pathway to the desired phenotype.

Accordingly, the aggregate cells are gently separated using a limiting amount of protease such as trypsin, or by mechanical trituration. They are than replated in high density cultures known as micromass cultures. Briefly, the cell clumps are suspended at about $6 \times 10^7$ cells/mL in a medium containing ~10% serum, and plated at 50 μL/well (filling the bottom ¼$^{th}$ of each well) in a 96-well plate, precoated with a suitable matrix such as gelatin. After 2 hours, the cells will adhere to one another, forming cell plugs. At this point, an additional 200 μL of medium is added, and the cells are cultured, changing medium daily if necessary because of the high density. The chondrocytes synthesize abundant matrix that cements the cell clusters together.

The cell clusters are then cultured with the mixture of differentiation factors for a period sufficient to cause selection or outgrowth of the desired phenotype (perhaps 1 or 2 weeks). As a pilot study, factors are studied in functional groups—for example, mixtures of TGFβs, GDFs, and BMPs are made, and tested for their ability to drive chondrocyte differentiation in various combinations with other groups, IHH, PTHrP, bFGF, and ascorbic acid. Concentration ranges for initial testing are 10-100 ng/mL for BMPs. GDFs, and TGFβs; 10-100 nM for PTHrP, and 0.1 to 1 mM for IHH. After analysis of the cells according to their phenotypic markers, as described in the next section, the groups unnecessary for differentiation are eliminated, and the important groups are dissected into their individual components. After several iterations, a minimal component mixture is determined, containing a particular factor or a cocktail of 2, 3, or more factors that generates the desired phenotype.

Other ligands or antibodies that bind the same receptors can be considered equivalents to any of the receptor ligands referred to in this disclosure.

Transforming growth factors beta (TGFβ) regulate various aspects of embryonic development and are expressed in the environment of sympathoadrenal progenitor cells (Wall et al., Curr. Opin. Genet. Dev. 4:517, 1994). In some systems. TGFβ regulates expression of parathyroid hormone-related protein (PTHrP) (Pateder et al., J. Cell Physiol. 188:343, 2001). BMPs and growth and differentiation factors (GDFs) are believed to play a central role during skeletogenesis, including joint formation (Francis-West et al., Cell Tissue Res 1296: 111, 1999). Indian hedgehog (IHH) is an essential component of mechanotransduction complex to stimulate chondrocyte proliferation (Wu et al., J. Biol. Chem. 276:35290, 2001). During endochondral ossification, two secreted signals, IHH and PTHrP are believed to form a negative feedback loop regulating the onset of hypertrophic differentiation of chondrocytes. Bone morphogenetic proteins (BMP) are thought to be mediators of signaling pathways for the patterning of skeletal elements and mechanisms for the induction of cartilage and bone formation. (Hoffmann et al., Crit. Rev. Eukaryot. Gene Expr. 11:23, 2001). BMPs have been implicated as potential interactors of the IHH/PTHrP feedback loop (Minina et al., Development 128:4523, 2001). BMPs may very well interact with IHH and PTHrP to coordinate chondrocyte proliferation and differentiation.

pPS-derived chondrocytes obtained according to this strategy may contain a high proportion of progenitor cells. When this is the case, the cells can be driven further down the differentiation pathway by culturing for an additional period with chondrocyte maturation factors. Candidates for effective cocktails of maturation factors include the differentiation factors listed above, in combination with growth factors such as insulin-like growth factor (IGF) and insulin.

Characteristics of Differentiated Cells

Cells can be characterized according to a number of phenotypic criteria. The criteria include but are not limited to microscopic observation of morphological features, detection or quantitation of expressed cell markers, functional criteria measurable in vitro, and behavior upon infusion into a host animal.

Phenotypic Markers

Cells of this invention can be characterized according to whether they express phenotypic markers characteristic of chondrocytes.

Type II collagen and aggrecan can be used as specific markers for cells that model articular cartilage. Cultures are also screened for the absence of elastin and Type I collagen, markers of elastic cartilage and fibrocartilage, respectively. Cultures can also be screened for the absence of Type X collagen and osteocalcin, markers of hypertrophic cartilage and bone, respectively, which could indicate a transient chondrocyte phenotype generated during the progression of endochondral bone formation. A table of commercially available antibodies for these human markers is shown below.

Tissue-specific markers can be detected using any suitable immunological technique—such as flow immunocytochemistry for cell-surface markers, or immunohistochemistry (for example, of fixed cells or tissue sections) for intracellular or cell-surface markers. A detailed method for flow cytometry analysis is provided in Gallacher et al., Blood 96:1740, 2000. Expression of a cell-surface antigen is defined as positive if a significantly detectable amount of antibody will bind to the antigen in a standard immunocytochemistry or flow cytometry assay, optionally after fixation of the cells, and optionally using a labeled secondary antibody or other conjugate to amplify labeling. Possible sources of specific antibody are shown in Table 1.

TABLE 1

Commercial Sources of Antibody
to Connective Tissue Markers

| Antibody | Source |
|---|---|
| Type I collagen | Chemicon, cat. # AB758 |
| Type II collagen | Chemicon, cat # AB761 |
| Type X collagen | RDI, cat # RDI-COLL10abr |
| Elastin | Chemicon, cat # AB2043 |
| Osteocalcin | Biomed. Tech. Inc., cat # BT593 |
| Aggrecan | BioTrend, cat # 0195-8050 |

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for particular markers listed in this disclosure can be obtained from public databases such as GenBank.

To facilitate engraftment, it is beneficial to maximize the proportion of cells in the population that have the characteristics of chondrocytes or their precursors, by refining the mixture of differentiation factors, culture conditions, and timing and following these markers. Populations in which at least 5% of the cells synthesize either Type II collagen or aggrecan, or both, may well be workable if the other cells in the population are inert, or play other roles in connective tissue (such as fibroblasts or mesenchymal cells). Populations enriched to the point where at least 25% of the cells synthesize either Type II collagen or aggrecan would be more efficacious in a number of contexts.

For therapeutic applications relating to cartilage regeneration, it is usually desirable to minimize the ability of the cell population to form elastic cartilage, fibrocartilage, hypertrophic cartilage and bone. This means that the proportion of cells synthesizing Type I collagen, Type X collagen, or osteocalcin (alone or in combination) is as low as possible, preferably below $1/5^{th}$ of the cells staining positive for Type II collagen or aggrecan, or less than 1%. Also desirable are populations with a low residual proportion of undifferentiated pPS cells. Preferred populations are less than 1%, or 0.2% SSEA-4+ve, Oct-4+ve, or positive for expression of endogenous telomerase reverse transcriptase.

Animal Model Experiments

Of considerable interest for development of chondrocytes for clinical application is the ability of cell populations to model cartilage and restore joint function in a host. Reconstitution of chondrocyte function can be tested using several well-established animal models.

Pilot experiments can be conducted using a model in which 6 mm holes are put in the external ear of the rabbit, leaving the adherent skin intact. Matrixes seeded with chondrocytes are then implanted, and the animals are monitored for hole closure (ten Koppel et al., Biomaterials 22:1407, 2001).

Alternatively, full thickness defects can be created in the weight bearing surface of the medial femoral chondyle of femora in rabbits (Grigolo et al., Biomaterials 22:2417, 2001). The wounds are repaired using chondrocytes seeded on a biomaterial, or pulled as a multicellular aggregate from the micromass culture. A membrane such as a piece of the periosteum or facia may be used to fold the implant in place, or matrix implants can be held in place with surgical dart. The full-thickness defect allows blood to seep into the site from the marrow cavity, creating a clot that contains endogenous stem cells. Rather than the medial chondyle, the work can be done with a defect created in the trochlear groove. This is a non-weight-bearing site, and implants are not dislodged as easily as from the medial chondyle.

Histologic samples from the treatment site are examined 1-6 months after surgery for population with the implant cells and cartilage deposits. This includes immunostaining for Type II collagen and aggrecan. Important morphological characteristics of the implant include cartilage thickness, smooth articular surface, and integration of the implant and endogenous cartilage at the borders of the defect. Long-term stability of the implant can be verified at the 12 month point.

As another option, a partial thickness defect can be created that doesn't penetrate the underlying bone or marrow cavity (Hunziker et al., Clin. Orthop. 391 Supp:S171, 2001). This type of defect serves as a model for osteoarthritis. Another model for osteoarthritis involves injection of estradiol into the knee joint of ovarectomized rabbits, causing loss of condyle surface congruity that resemble the defects observed in osteoarthritis in humans (Tsai et al., Clin Orthoop. 291:295, 1993).

Genetic Modification of Differentiated Cells

Many of the chondrocyte populations of this invention have a substantial proliferation capacity. If desired, the replication capacity can be further enhanced by increasing the level of telomerase reverse transcriptase (TERT) in the cell, either by increasing transcription from the endogenous gene, or introducing a transgene. Particularly suitable is the catalytic component of human telomerase (hTERT), provided in International Patent Application WO 98/14592. Transfection and expression of telomerase in human cells is described in Bodnar et al., Science 279:349, 1998 and Jiang et al., Nat. Genet. 21:111, 1999. Genetically altered cells can be assessed for hTERT expression by RT-PCR, telomerase activity (TRAP assay), immunocytochemical staining for hTERT, or replicative capacity, according to standard methods. Other methods of immortalizing cells are also contemplated, such as transforming the cells with DNA encoding myc, the SV40 large T antigen, or MOT-2 (U.S. Pat. No. 5,869,243, International Patent Applications WO 97/32972 and WO 01/23555).

If desired, the cells of this invention can be prepared or further treated to remove undifferentiated cells in vitro, or to safeguard against revertants in vivo. One way of depleting undifferentiated stem cells from the population is to transfect the population with a vector in which an effector gene under control of a promoter that causes preferential expression in undifferentiated cells—such as the TERT promoter or the OCT-4 promoter. The effector gene may be a reporter to guide cell sorting, such as green fluorescent protein. The effector may be directly lytic to the cell, encoding, for example, a toxin, or a mediator of apoptosis, such as caspase (Shinoura et al, Cancer Gene Ther. 7:739, 2000). The effector gene may have the effect of rendering the cell susceptible to toxic effects of an external agent, such as an antibody or a prodrug. Exemplary is a herpes simplex thymidine kinase (tk) gene, which causes cells in which it is expressed to be susceptible to ganciclovir (U.S. Ser. No. 60/253,443). Alternatively, the effector can cause cell surface expression of a foreign determinant that makes any cells that revert to an undifferentiated phenotype susceptible to naturally occurring antibody in vivo (U.S. Ser. No. 60/253,357).

Use of Chondrocytes in Research and Clinical Therapy

This invention provides a method to produce large numbers of chondrocytes for a variety of important research, development, and commercial purposes.

The cells of this invention can be used to prepare a cDNA library relatively uncontaminated with cDNA preferentially expressed in cells from other lineages. The differentiated cells of this invention can also be used to prepare monoclonal or polyclonal antibodies that are specific for markers of chondrocytes and their derivatives, according to standard methods.

Of particular interest are use of the compositions of this invention for drug development and clinical therapy.

Drug Screening

The cells of this invention can be used to screen for factors (such as solvents, small molecule drugs, peptides, polynucleotides) or environmental conditions (such as culture conditions or manipulation) that affect the characteristics of both chondrocyte precursors and mature chondrocytes.

In one example, pPS cells (undifferentiated or initiated into the differentiation paradigm) are used to screen factors that promote maturation into chondrocytes, or promote proliferation and maintenance of chondrocytes in long-term culture. For example, candidate maturation factors or growth factors are tested by adding them to cells in different wells, and then determining any phenotypic change that results, according to desirable criteria for further culture and use of the cells. This can lead to improved derivation and culture methods not only for pPS derived chondrocytes, but for chondrocytes and their progenitors isolated from cartilage.

Another example is the use of chondrocytes to measure the effect of small molecule drugs that have the potential to affect chondrocyte activity in their role of shaping or remodeling cartilage. To this end, the cells can be combined with test compounds in vitro, and the effect of the compound on gene expression or protein synthesis can be determined. The screening can also be done in vivo by measuring the effect of the compound on the behavior of the cells in an animal model.

Other screening methods of this invention relate to the testing of pharmaceutical compounds for a potential effect on chondrocyte growth, development, or toxicity. This type of screening is appropriate not only when the compound is designed to have a pharmacological effect on chondrocytes themselves, but also to test for chondrocyte-related side-effects of compounds designed for a primary pharmacological effect elsewhere.

The reader is referred generally to the standard textbook "In vitro Methods in Pharmaceutical Research", Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in "In vitro Methods in Pharmaceutical Research," Academic Press, 1997) for further elaboration.

Chondrocytes in Clinical Therapy

This invention also provides for the use of chondrocyte precursor cells and their derivatives to retain or restore cartilage-containing musculoskeletal structures in a patient in need of such therapy. Any condition leading to impairment of joint mobility may be considered. Included is damage caused by percussive trauma, and sports injuries. The cells of the invention can also be considered for treatment of degenerative conditions, such as osteoarthritis and rheumatoid arthritis to restore lost function, providing that the primary pathology causing the degeneration is sufficiently well controlled. Also contemplated is the use of the cells of this invention for cosmetic surgery, including but not limited to surgery of the proboscis. See *Aesthetic Reconstruction of the Nose*, by G. C. Burget & F. J. Menick, Mosby Year Book 1994; *The Nose*, by Nikolay Gogol et al., David R. Godine publisher, 1993; and Yoo et al., J. Urol. 162:1119, 1999.

Chondrocytes made according to this invention can be prepared for administration in a cell suspension (using trypsin or collagenase, if necessary), using a physiologically compatible excipient: for example, an isotonic medium containing 1.25 mL gentomycin sulfate (70 µmol/L), 2.0 mL amphotericin (2.2 µmol/L), 7.5 mL L-ascorbic acid (300 µmol/L), 25 mL blood serum or its equivalent (to 10% vol/vol) in 300 mL. During the chondrocyte transplantation procedure, the damaged cartilage is covered with a cap secured by mechanical or adhesive retention means, such as a biocompatible fibrin glue. The cultured chondrocyte cells in transplant excipient (about 0.6 mL containing about $10 \times 10^6$ chondrocytes) are injected under the covering cap using a ~23 gauge needle.

Alternatively, the chondrocytes are prepared by growing on a matrix formed, for example, using a collagen membrane (commercially available collagen matrix pads are available from Ed. Geistlich Sohne, Switzerland). A few days before transplant, the growth media is exchanged for a transplant excipient. During surgery, the chondrocyte cell-loaded matrix is glued into the area of damaged cartilage using a biocompatible adhesive. The covering cap or matrix remains place for a period of time sufficient to allow for cartilage repair, and is then absorbed or resorbed by the body, for example, within two to three months from implantation. Further elaboration of the design and use of resorbable caps and matrices can be found in International patent publication WO 01/08610.

As always, the ultimate responsibility for patient selection, mode of administration, and choice of support structures and surgical options is the responsibility of the managing clinician.

For purposes of commercial distribution, chondrocytes of this invention are typically supplied in the form of a pharmaceutical composition, comprising an isotonic excipient prepared under sufficiently sterile conditions for human administration. For general principles in medicinal formulation of cell compositions, the reader is referred to *Cell Therapy: Stem Cell Transplantation, Gene Therapy, and Cellular Immunotherapy*, by G. Morstyn & W. Sheridan eds. Cambridge University Press, 1996.

The composition may also contain a matrix for keeping the chondrocytes in place during the first few months following therapy Absorbable biomaterials save the necessity of subsequent surgical removal. Besides the collagen matrix pads described in WO 01/086101, other possible matrixes include bioresorbable polymer fleece matrices (Rudert et al., Cells Tissues Organs 167:95, 2000); hyaluronan derivatives (Grigolo et al., Biomaterials 22:2417, 2001); sponge made from poly(L-lactide-epsilon-caprolactone) (Honda et al., J. Oral Maxillofac. Surg. 58:767, 2000), and collagen-fibrin matrices (Clin. Exp. Rheumatol. 18:13, 2000).

The composition or device is optionally packaged in a suitable container with written instructions for a desired purpose, such as the reconstruction of joint cartilage or cosmetic surgery.

It is understood that certain adaptations of the invention described in this disclosure as a matter of routine optimization for those skilled in the art, and can be implemented without departing from the spirit of the invention, or the scope of the appended claims.

What is claimed as the invention is:

1. A method of screening a compound for an effect on cultured chondrocytes, comprising:
    a) providing primate pluripotent stem cells which express SSEA3, SSEA4, Tra-1-60 and Tra-1-81;
    b) culturing the primate pluripotent stem cells which express SSEA3, SSEA4, Tra-1-60 and Tra-1-81 in a medium comprising one or more of transforming growth factor (TGF), fibroblast growth factor (FGF), growth differentiation factor (GDF), bone morphogenic protein (BMP), hedgehog protein, L-ascorbic acid and parathyroid hormone related protein to produce cultured chondrocytes;
    c) contacting the cultured chondrocytes with the compound; and
    d) observing a change in the cultured chondrocytes.

2. The method of claim 1, wherein the compound is a peptide.

3. The method of claim 1, wherein the compound is an oligonucleotide.

4. The method of claim 1, wherein the compound is a toxin.

5. The method of claim 1, wherein the compound is a small molecule.

6. The method of claim 1, wherein the compound is a solvent.

7. The method of claim 1, wherein the cultured chondrocytes have chromosomal DNA that is at least 99.6% identical to the chromosomal DNA of an established line of cells which express SSEA3, SSEA4, Tra-1-60 and Tra-1-81.

8. The method of claim 1, wherein the cultured chondrocytes have chromosomal DNA that is at least 99.7% identical to the chromosomal DNA of an established line of cells which express SSEA3, SSEA4, Tra-1-60 and Tra-1-81.

9. The method of claim 1, wherein the cultured chondrocytes have chromosomal DNA that is at least 99.8% identical to the chromosomal DNA of an established line of cells which express SSEA3, SSEA4, Tra-1-60 and Tra-1-81.

10. The method of claim 1, wherein the cultured chondrocytes have chromosomal DNA that is at least 99.9% identical to the chromosomal DNA of an established line of cells which express SSEA3, SSEA4, Tra-1-60 and Tra-1-81.

11. The method of claim 1, wherein the cultured chondrocytes have chromosomal DNA that is genetically identical to the chromosomal DNA of an established line of cells which express SSEA3, SSEA4, Tra-1-60 and Tra-1-81.

12. A method of screening a compound for an effect on cultured cells expressing collagen type II and/or aggrecan chondrocytes, comprising:
    a) providing primate pluripotent stem cells which express SSEA3, SSEA4, Tra-1-60 and Tra-1-81;
    b) culturing the primate pluripotent stem cells which express SSEA3, SSEA4, Tra-1-60 and Tra-1-81 in a medium comprising one or more of transforming growth factor (TGF), fibroblast growth factor (FGF), growth differentiation factor (GDF), bone morphogenic protein (BMP), hedgehog protein, L-ascorbic acid and parathyroid hormone related protein to produce cultured cells expressing collagen type II and/or aggrecan;
    c) contacting the cultured cells expressing collagen type II and/or aggrecan with the compound; and
    d) observing a change in the cultured cells expressing collagen type II and/or aggrecan.

13. The method of claim 12, wherein the compound is a peptide.

14. The method of claim 12, wherein the compound is an oligonucleotide.

15. The method of claim 12, wherein the compound is a toxin.

16. The method of claim 12, wherein the compound is a small molecule.

17. The method of claim 12, wherein the compound is a solvent.

18. The method of claim 12, wherein the cultured collagen type II expressing chondrocytes have chromosomal DNA that is at least 99.6% identical to the chromosomal DNA of an established line of cells which express SSEA3, SSEA4, Tra-1-60 and Tra-1-81.

19. The method of claim 12, wherein the cultured collagen type II expressing chondrocytes have chromosomal DNA that is at least 99.7% identical to the chromosomal DNA of an established line of cells which express SSEA3, SSEA4, Tra-1-60 and Tra-1-81.

20. The method of claim 12, wherein the cultured collagen type II expressing chondrocytes have chromosomal DNA that is at least 99.8% identical to the chromosomal DNA of an established line of cells which express SSEA3, SSEA4, Tra-1-60 and Tra-1-81.

21. The method of claim 12, wherein the cultured collagen type II expressing chondrocytes have chromosomal DNA that is at least 99.9% identical to the chromosomal DNA of an established line of cells which express SSEA3, SSEA4, Tra-1-60 and Tra-1-81.

22. The method of claim 12, wherein the cultured collagen type II expressing chondrocytes have chromosomal DNA that is identical to the chromosomal DNA of an established line of cells which express SSEA3, SSEA4, Tra-1-60 and Tra-1-81.

* * * * *